US010131944B2

(12) United States Patent
Bernick et al.

(10) Patent No.: US 10,131,944 B2
(45) Date of Patent: Nov. 20, 2018

(54) MOLECULAR ADAPTER FOR CAPTURE AND MANIPULATION OF TRANSFER RNA

(71) Applicant: The Regents of the University of California, Oakland, CA (US)

(72) Inventors: David Bernick, Santa Cruz, CA (US); Andrew Smith, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 25 days.

(21) Appl. No.: 15/128,971

(22) PCT Filed: Mar. 24, 2015

(86) PCT No.: PCT/US2015/022329
§ 371 (c)(1),
(2) Date: Sep. 24, 2016

(87) PCT Pub. No.: WO2015/148567
PCT Pub. Date: Oct. 1, 2015

(65) Prior Publication Data
US 2017/0218439 A1 Aug. 3, 2017

Related U.S. Application Data

(60) Provisional application No. 61/969,381, filed on Mar. 24, 2014.

(51) Int. Cl.
G01N 27/447 (2006.01)
G01N 27/403 (2006.01)
(Continued)

(52) U.S. Cl.
CPC .......... *C12Q 1/6869* (2013.01); *C07H 21/02* (2013.01); *C07H 21/04* (2013.01);
(Continued)

(58) Field of Classification Search
CPC ......... G01N 27/447–27/44795; G01N 33/487; G01N 33/48721; G01N 33/48728;
(Continued)

(56) References Cited

U.S. PATENT DOCUMENTS 5,795,782 A 8/1998 Church et al.
RE43,097 E 1/2012 Lloyd et al.
(Continued)

OTHER PUBLICATIONS

International Preliminary Report on Patentability dated Sep. 27, 2016, issued in International Application No. PCT/US2015/022329, 9 pages.
(Continued)

*Primary Examiner* — Bach T Dinh
(74) *Attorney, Agent, or Firm* — Kilpatrick Townsend & Stockton LLP

(57) ABSTRACT

The invention also encompasses novel structures and methods comprising providing a molecular adapter for capture and manipulation of transfer RNA. The adaptor is bound to a tRNA molecule. The adaptor may be a cholesterol-linked DNA adapter oligonucleotide. The invention is useful in sequencing, identification, manipulation and modification of tRNA.

14 Claims, 6 Drawing Sheets

Figure 1:
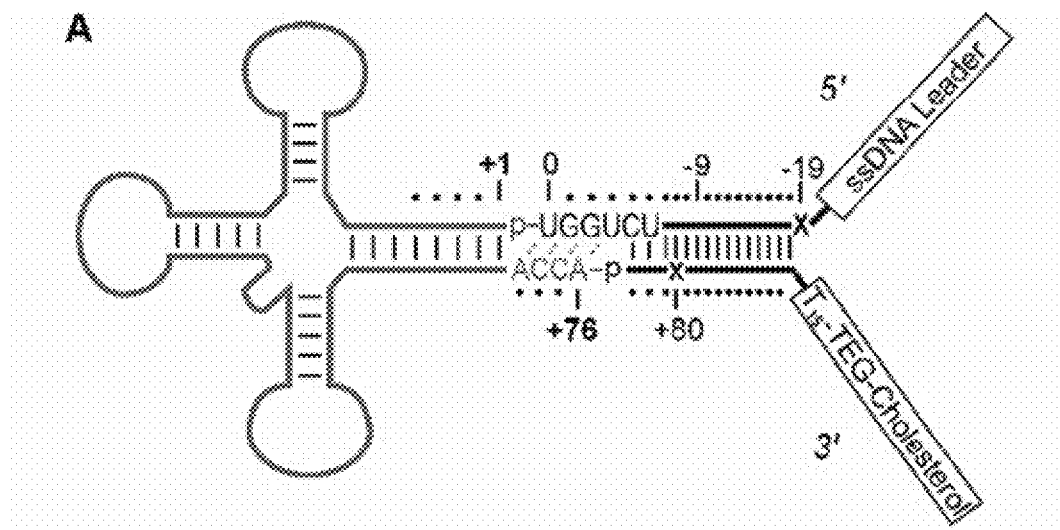
Figure 1:
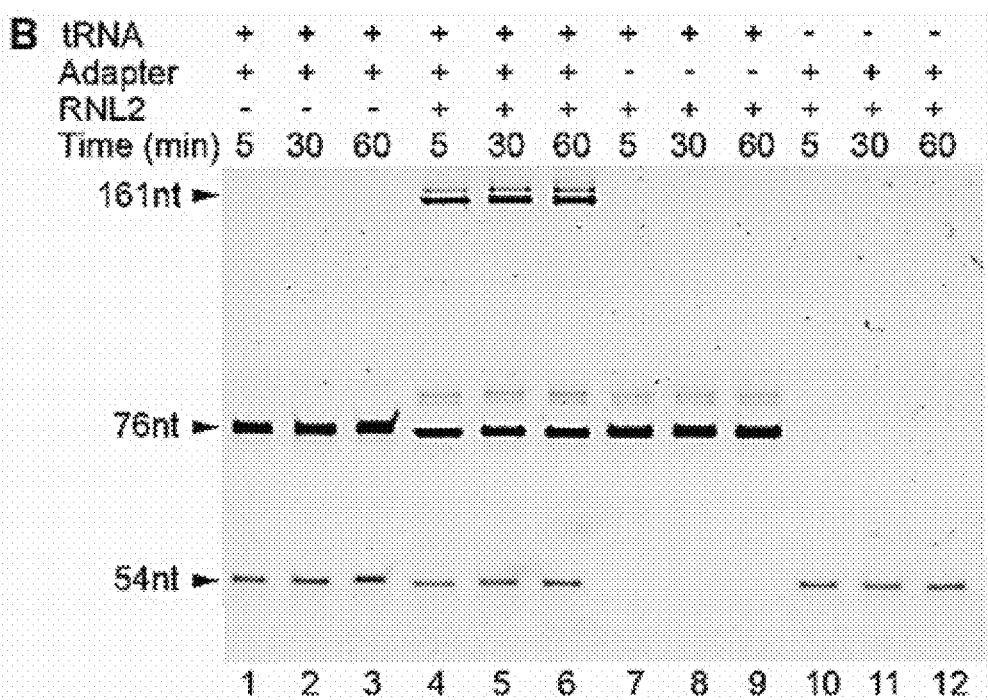

Specification includes a Sequence Listing.

(51) Int. Cl.
  C12Q 1/6869     (2018.01)
  C07H 21/02      (2006.01)
  C07H 21/04      (2006.01)
  G01N 33/487     (2006.01)

(52) U.S. Cl.
  CPC ... G01N 27/4473 (2013.01); G01N 33/48721 (2013.01); *H05K 999/99* (2013.01)

(58) Field of Classification Search
  CPC ........ B01D 57/00–57/02; C02F 1/4696; B81B 1/00–1/008
  USPC ................ 204/450–470, 546–550, 600–621, 204/643–645
  See application file for complete search history.

(56) References Cited

U.S. PATENT DOCUMENTS

| | | | |
|---|---|---|---|
| 2011/0009606 A1 | 1/2011 | Laikhter et al. | |
| 2012/0244525 A1 | 9/2012 | Hendrickson et al. | |
| 2013/0130322 A1* | 5/2013 | Tuschl | C12N 9/93 435/91.3 |
| 2013/0327644 A1* | 12/2013 | Turner | C12Q 1/6869 204/543 |
| 2014/0186823 A1* | 7/2014 | Clarke | C07K 14/35 435/6.1 |

OTHER PUBLICATIONS

International Search Report dated Jul. 16, 2015, issued in International Application No. PCT/US2015/022329, 3 pages.
Thermo Scientific, "Anneal complementary pairs of oligonucleotides," 2009, TECG TIP 17 #45, pp. 1-2. Retrieved from the Internet:<https://tools.lifetechnologies.com/content/sfs/brochures/TR0045-Anneal-Oligos.pdf> on Jun. 22, 2015 (Jun. 22, 2015).
Ayub et al., "Individual RNA base recognition in immobilized oligonucleotides using a protein nanopore", Nano letters 12(11), 2012, 5637-5643.
Butler et al., "Single-molecule DNA detection with an engineered MspA protein nanopore", Proceedings of the National Academy of Sciences 105(52), 2008, 20647-20652.
Chang et al., "Electronic signatures of all four DNA nucleosides in a tunneling gap", Nano letters 10(3), 2010, 1070-1075.
Clarke et al., "Continuous base identification for single-molecule nanopore DNA sequencing.", Nature Nanotechnology 4(4), Apr. 2009, 265-270.
Faller et al., "The structure of a mycobacterial outer-membrane channel", Science 303(5661), 2004, 1189-1192.
Garaj et al., "Graphene as a subnanometre trans-electrode membrane", Nature 467(7312), Sep. 9, 2010, pp. 190-193.
Kasianowicz et al., "Characterization of individual polynucleotide molecules using a membrane channel", Proceedings of the National Academy of Sciences 93(24), 1996, 13770-13773.
Laszlo et al., "Detection and mapping of 5-methylcytosine and 5-hydroxymethylcytosine with nanopore MspA", Proceedings of the National Academy of Sciences 110(47), 2013, 18904-18909.
Lieberman et al., "Processive replication of single DNA molecules in a nanopore catalyzed by phi29 DNA polymerase", Journal of the American Chemical Society 132(50), 2010, 17961-17972.
Manrao et al., "Nucleotide discrimination with DNA immobilized in the MspA nanopore", PloS one 6(10), 2011, e25723.
Marty et al., "Structural characterization of cationic lipid-tRNA complexes", Nucleic acids research 37(15), 2009, 5197-5207.
McNally et al., "Optical recognition of converted DNA nucleotides for single-molecule DNA sequencing using nanopore arrays", Nano letters 10(6), 2010, 2237-2244.
Purnell et al., "Nucleotide identification and orientation discrimination of DNA homopolymers immobilized in a protein nanopore", Nano letters 8(9), 2008, 3029-3034.
Rusk, "Cheap Third-Generation Sequencing", Nature Methods 6 (4), Apr. 1, 2009, 244-245.
Sadki et al., "Embedding a carbon nanotube across the diameter of a solid state nanopore", Journal of Vacuum Science & Technology B, Nanotechnology and Microelectronics: Materials, Processing, Measurement, and Phenomena 29(5), 2011.
Schreiber et al., "Error rates for nanopore discrimination among cytosine, methylcytosine, and hydroxymethylcytosine along individual DNA strands", Proceedings of the National Academy of Sciences 110(47), 2013, 18910-18915.
Smith et al., "Capture, unfolding, and detection of individual tRNA molecules using a nanopore device", Frontiers in bioengineering and biotechnology 3, 2015, 1-23.
Soni et al., "Synchronous optical and electrical detection of biomolecules traversing through solid-state nanopores", Review of Scientific Instruments 81(1), 2010, 014301.
Sprinzl et al., "Compilation of tRNA Sequences and Sequences of tRNA Genes", Nucleic Acids Research 24(1), 1996, 68-72.
Stoddart et al., "Multiple Base-Recognition Sites in a Biological Nanopore: Two Heads are Better than One", Angewandte Chemie International Edition 49(3), 2010, 556-559.
Stoddart et al., "Single-nucleotide discrimination in immobilized DNA oligonucleotides with a biological nanopore", Proceedings of the National Academy of Sciences 106(19), 2009, 7702-7707.
Winters-Hilt et al., "Highly accurate classification of Watson-Crick basepairs on termini of single DNA molecules", Biophysical Journal 84(2), 2003, 967-976.

* cited by examiner

MOLECULAR ADAPTER FOR CAPTURE AND MANIPULATION OF TRANSFER RNA

RELATION TO OTHER APPLICATIONS

This application claims priority to and the benefit of U.S. provisional application 61/969,381 filed 24 Mar. 2014, titled Molecular adapter for capture and manipulation of transfer RNA. This application is incorporated by reference for all purposes.

GOVERNMENT SPONSORSHIP

None
A sequence listing text (.txt) file is submitted herewith under 37 CFR. 1.821(c) and is hereby incorporated by reference in its entirely. The details of the file as required under 37 CFR. 1.52(e)(5) and 37 CFR 1.77(b)(5) are as follows: Name of file is 3_SC2014_725_PCT_SeqList_ST25_ok_.txt; date of creation is May 12, 2015; size is 1.70 KB (1,749 bytes). The content of the sequence listing information recorded in computer readable form is identical to the written sequence listing (if any) and identical to the sequence information provided with the original filed application and the priority application, and contains no new matter.

FIELD OF THE INVENTION

Novel structures comprising a tRNA bound to cholesterol-linked DNA adapter oligonucleotides useful in sequencing, identification, manipulation and modification of tRNA. The invention further encompasses methods for using a nanopore to detect individual tRNA molecules.

BACKGROUND tRNA is notoriously difficult to manipulate. Sequencing of tRNA presents various problems because of complex and tightly bound secondary structure and protein association. Despite the difficulties in sequencing tRNAs, the have been extensively sequenced and their structures are well known, see Mathias Sprinzl et al., Compilation of tRNA Sequences and Sequences of tRNA Genes Nucl. Acids Res. (1996) 24 (1): 68-72, hereby incorporated by reference.

Current methods for analysis of tRNAs, and RNA in general, include RNAseq, microarray, and mass spectrometry. These methods are proven tools for detection of novel tRNAs and global tRNA expression patterns (Chan et al. 2011; Dittmar et al. 2006). However, each method has limitations. High throughput RNA sequencing (RNASeq) methods require extensive library preparation, including PCR amplification, to prepare cellular RNA for sequencing. A reverse transcription (RT) step is necessary to copy the original RNA sequence to cDNA, which results in loss of the original RNA strand. Additionally, the RT step is impeded by the occurrence of structure and nucleotide modifications, which are both commonly found in tRNAs. These "RTstops" result in truncated cDNA.

Nanopore sequencing of polynucleotides (including ribopolynuicleotides) works on the principle that when a nanopore is immersed in an ionic solution and a voltage is applied across it, and when a molecule such as a nucleotide passes through (or near) a nanopore, it creates a characteristic perturbation of the current signature passing between two sides of the nanopore. Nanopores may be used to identify individual DNA bases as they pass through the nanopore. Such an approach has been demonstrated and commercialized by Oxford Nanopore Technologies. Using this technology a single molecule of DNA can be sequenced directly using a nanopore, without the need for an intervening PCR amplification or chemical labelling step.

Nanopore sensors are single molecule based and would allow for examination of several thousand individual tRNA molecules in a single experiment. Biological nanometer scale pores, such as αHL, were proposed as single molecule sensors for nucleic acids almost twenty years ago (Kasianowicz et al. 1996). In concept, the nucleotide sequence of an individual molecule could be read by observing changes in ionic current as the linearized strand is electrophoresed through the nanopore aperture. Recent developments in sensing DNA have coupled an enzyme to regulate DNA movement in single nucleotide steps through a nanopore, which produced ionic current traces that provide a single base readout of DNA sequence (Cherf et al. 2012; Manrao et al. 2012). While no such result has been demonstrated for RNA, work examining immobilized RNA in an engineered αHL pore indicates that an appropriately sensitive nanopore can discriminate between the four canonical RNA nucleotides and specific modified ribonucleotides (Ayub and Bayley 2012).

Experiments by the present inventors and others have shown that DNA cytosine modifications can be detected with high confidence from individual nanopore reads of chemically synthesized DNA (Schreiber et al. 2013; Laszlo et al. 2013). By extension, these results suggest that nanopore sensors could detect sub-molecular features of tRNA, including nucleotide modifications, if tRNAs can be mechanically unfolded and electrically motivated to pass through the pore.

With this in mind the present inventors sought to develop a mechanism to specifically capture tRNA molecules, promote their mechanical unfolding, and initiate threading of the linearized strand through the nanopore lumen.

SHORT DESCRIPTION OF THE INVENTION

The method of the invention comprises a mechanism to specifically capture tRNA molecules, promote their mechanical unfolding, and initiate threading of the linearized strand through the nanopore lumen.

The invention includes attaching DNA or RNA "handles" to a tRNA molecule. These handles provide a means of manipulating the tRNA molecule, including unfolding its structure and acting as targets for attaching other molecules to the tRNA.

The present invention discloses a double stranded oligonucleotide adapter that can be enzymatically ligated to biological tRNA. The two strands of the adapter act to locally concentrate adapted tRNA at the bilayer and to initiate strand threading through the nanopore.

The invention also encompasses methods employing nanopores and the use of nanopores for determining the structure and sequence of tRNA.

The invention also encompasses novel structures and methods comprising providing a molecular adapter for capture and manipulation of transfer RNA. The adaptor is bound to a tRNA molecule. The adaptor may be a cholesterol-linked DNA adapter oligonucleotide. The invention is useful in sequencing, identification, manipulation and modification of tRNA. The novel structures facilitate both concentrating of the adapted tRNA to the lipid bilayer of the nanopore device and efficient denaturation of the tRNA as it passes through the nanopore.

The cholesterol-linked DNA adapter oligonucleotides are bound to the tRNA by enzymatic ligation.

Additionally the cholesterol-linked DNA adapter oligonucleotides can function as loading sites for φ29 DNA polymerase.

Nanopores used in the invention may be of any type, biological or solid-state (inorganic). Suitable biological nanopores include, for example, Alpha hemolysin (αHL) and *Mycobacterium smegmatis* porin A (MspA).

SHORT DESCRIPTION OF THE FIGURES

FIG. 1. Shows a schematic diagram showing an exemplary tRNA adapter structure, and discloses the strategy for constructing adapter linked tRNA molecules for nanopore experiments. (A) The DNA/RNA chimeric adapter (black lines; RNA nucleotides black letters) was composed of a double stranded region and a four nucleotide RNA overhang (UGGU) ligated to the tRNA (cyan). The adapter specifically targets the conserved CCA tail of de-acylated, native tRNA. Phosphodiester bonds formed by enzymatic ligation between the tRNA and the adapter are indicated by dashes between the 3' terminal nucleotide and 5' phosphate (p) at ligation junctions. The boxed tail regions were a single stranded DNA (ssDNA) leader used for nanopore capture, and a poly(dT) region with a terminal TEG linked (triethylene glycol) cholesterol. This terminal TEG-cholesterol on the 3' adapter strand was designed to localize substrate at the lipid bilayer. Tails are not drawn to scale. The adapter nucleotides are numbered relative to the first and last nucleotide of a canonical tRNA. The X's indicate abasic positions. (B) Denaturing PAGE analysis of tRNA adapter ligation reaction (see Methods). Time points are in minutes. Lanes 13, control reaction with *S. cerevisiae* tRNA(phe) (76nt) and adapter (54nt leader strand), but absent RNA Ligase 2 (RNL2). Lanes 46, *S. cerevisiae* tRNA(phe) incubated with the adapter and RNL2. Lanes 79, control reaction with RNL2 but absent adapter. Lanes 1012, control reaction absent tRNA(phe). The 31 nt 3' adapter oligonucleotide stains poorly (not shown). All subsequent nanopore experiments were conducted with complete ligation products after gel purification (see Methods).

Figure 2:
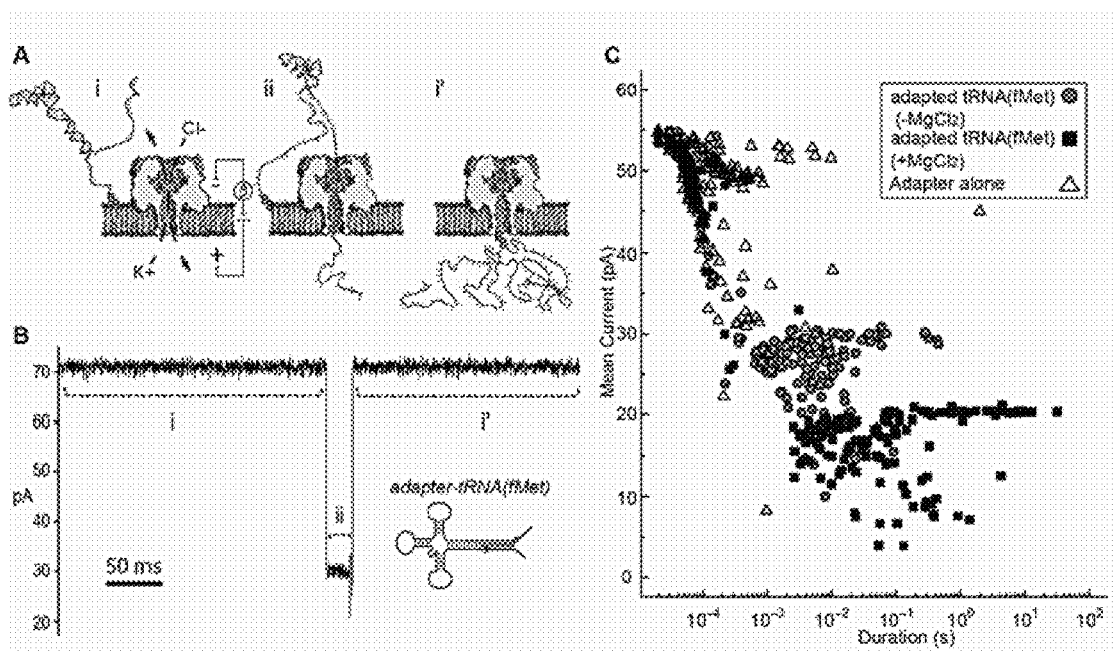

FIG. 2. Adapted tRNA dependent ionic current blockades observed during single channel αHL nanopore experiments. (A) cartoon illustration of the single channel nanopore apparatus and a proposed adapted tRNA translocation event. i) A constant voltage (trans side+) is applied across a single αHL nanopore (orange) embedded in a lipid bilayer (grey). ii) Electrophoretic capture of an adapted tRNA (cyan) results in a decrease in the measured ionic current through the nanopore. i') Return to open channel current when the tRNA clears the pore in the trans compartment. (B) An ionic current trace from a nanopore experiment with adapted *E. coli* tRNA fMet. Ionic current regions iii and i' in the trace (dashed lines) correspond to the proposed tRNA translocation event in panel A. The blockade event shown is typical of thousands of events observed during nanopore experiments with adapted tRNA fMet. (C) Nanopore blockade mean ionic current versus duration caused by adapted tRNA fMet in the presence or absence of Mg 2+. The mean current and duration of approximately two hundred events are shown for representative nanopore experiments with either adapted tRNA fMet (Mg 2+) (magenta circles) or adapted tRNA fMet (+Mg 2+) (blue squares). The adapter on its own (Mg 2+) (open triangles) was also examined as a negative control. In all cases, single channel αHL nanopore experiments were conducted at 180 mV (trans side+) with tRNA substrate at 0.5 nM in 0.3M KCl, 10 mM HEPES (pH 8.0), and +/5 mM MgCl2 (see Methods).

Figure 3:
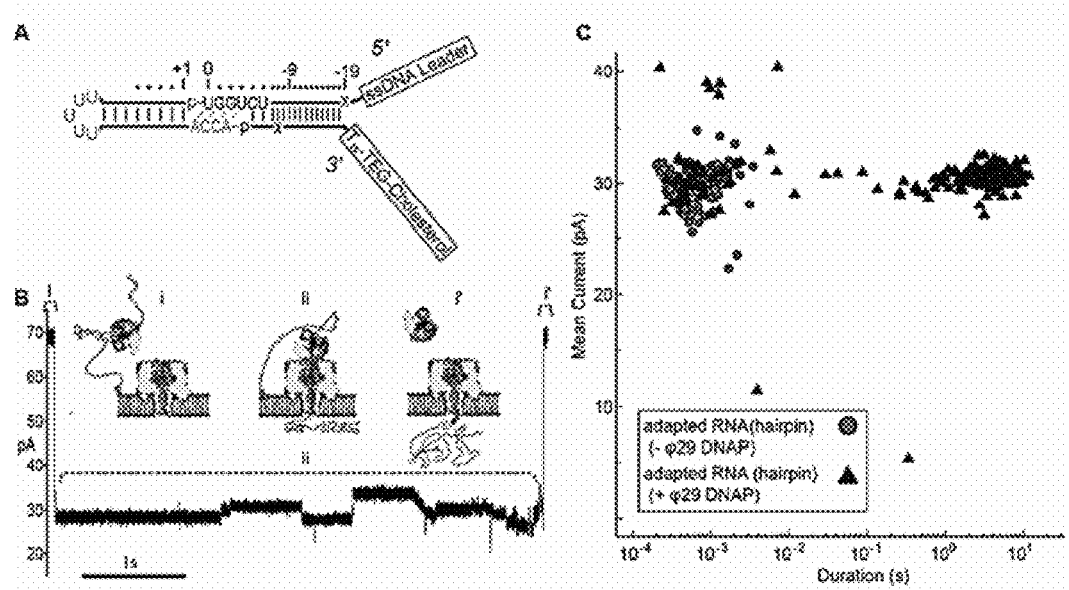

FIG. 3. Nanopore capture of adapted RNA complexed with non-catalytic φ29 DNAP. (A) Schematic of the synthetic RNA (hairpin) construct covalently attached to the adapter (black). This simple RNA hairpin is composed of a synthetic copy of the *E. coli* tRNA fMet acceptor stem linked by a five uracil loop. This RNA was enzymatically ligated to the adapter as described previously (see Methods). X's indicate 5' and 3' abasic residues in the adapter strands. (B) Representative ionic current trace during capture of an adapted RNA hairpin complexed with φ29 DNAP. φ29 DNAP (75 nM) and adapted RNA (hairpin) (0.5 nM) were added to cis side compartment which contained nanopore buffer absent Mg 2+ and amended with 1 mM EDTA (see Methods). The cartoons above the ionic current trace represent proposed steps during φ29 DNAP controlled translocation: i) open channel prior to capture of the adapted RNA::φ29 DNAP complex; ii) nanopore capture and translocation of adapted RNA bound to φ29 DNAP; i') return to open channel current when the RNA clears the pore into the trans compartment. (C) Mean ionic current versus duration for adapted RNA (hairpin) dependent blockades absent (circles) or present (triangles) φ29 DNAP. Approximately 200 events are shown for each condition from a representative single experiment.

Figure 4:
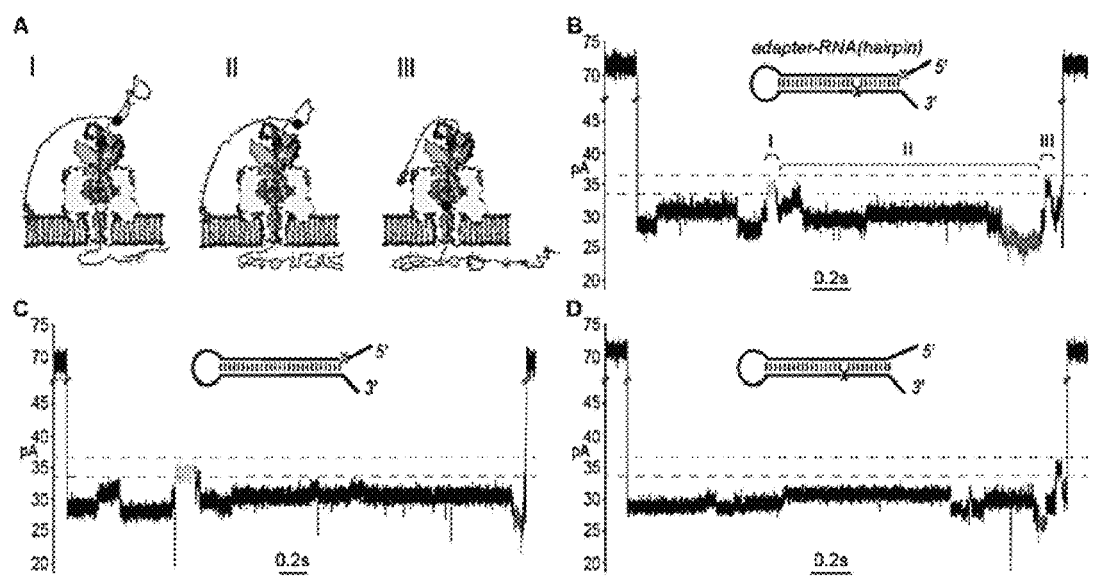

FIG. 4. End-to-end translocation of adapted RNA (hairpin) constructs through the αHL nanopore. (A) A cartoon model showing capture and translocation of an adapted RNA (hairpin) complexed with φ29 DNAP. The adapted RNA (hairpin) substrate is described in FIG. 3. I) Following capture of the 5' end of the adapter strand, the polynucleotide translocates through αH until the leading 5' abasic residue (blue circle) reaches pore limiting aperture. II) Translocation continues through the RNA portion of the adapted molecule. III) The trailing 3' abasic residue (red circle) reaches the pore limiting aperture after translocation of the RNA(hairpin). (B) A nanopore ionic current trace during translocation of an adapted RNA(hairpin) (inset), which corresponding to the cartoon in panel A. The event displays two high current marker regions characteristic of the 5' abasic residue (blue segment) and 3' abasic residue (red segment) built into the adapter. Translocation events that contained both leading and trailing markers were observed in ~27% of events with durations exceeding one second. The marker ionic current level was 33.536.5 pA (dashed gray lines) under the experimental conditions used (see Methods). (C) A nanopore ionic current trace during translocation of an adapted RNA(hairpin) (inset) bearing only the 5' abasic residue (5' mono-abasic adapted RNA). (D) A nanopore ionic current trace during translocation of an adapted RNA(hairpin) (inset) bearing only the 3' abasic residue (3' mono-abasic adapted RNA).

Figure 5:
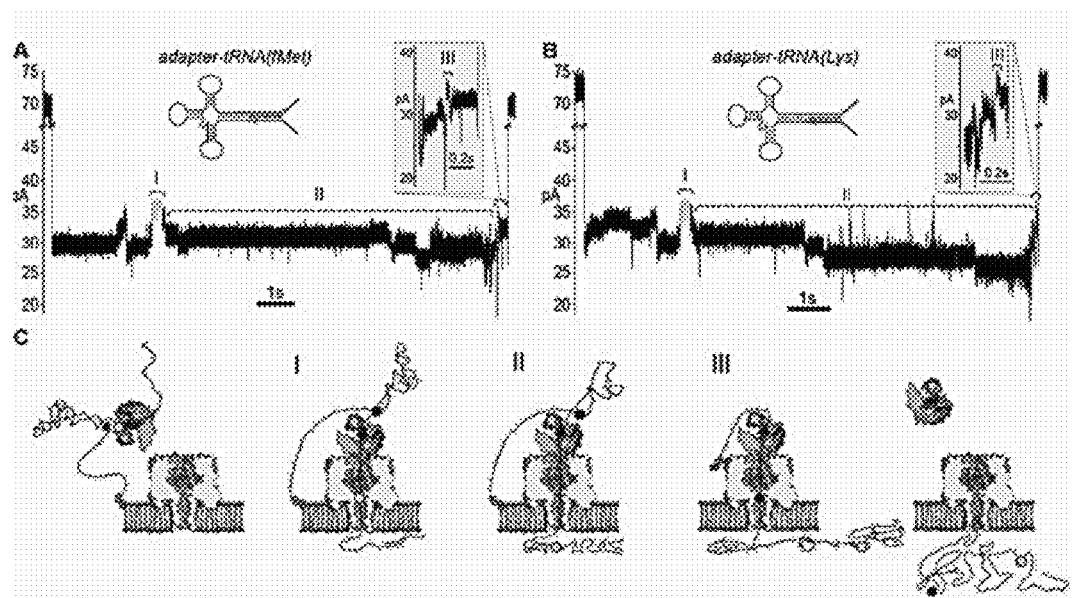

FIG. 5. Adapted *E. coli* tRNA fMet and tRNA Lys translocate through the αHL nanopore. (A) representative nanopore ionic current trace for adapted *E. coli* tRNA fMet (inset). The rate of translocation through the nanopore is controlled by φ29 DNAP (see FIG. 3). The leading high current marker (I, segment) and the trailing high current marker (III, red segment correspond to the 5' abasic residue and 3' abasic residue transiting the nanopore, as in FIG. 4B. Region II of the trace contains the portion of the nanopore signal associated with tRNA translocation. Translocation events that contained both 5' and 3' current markers were observed in ~20% of all events with durations exceeding one second. (B) A representative trace from nanopore experiments with adapted tRNA Lys. Details are the same as in panel A. (C) A cartoon model of an adapted tRNA as it transits the αHL nanopore. The panels to the left and right correspond to open channel before and after tRNA translocation (see FIG. 3). Roman numerals correspond to the roman numerals in panels A and B. I) Translocation of the leading adapter strand through αHL until the 5' abasic residue (circle) reaches the pore limiting aperture. II) Translocation of the tRNA portion of the adapted molecule. III Translocation of the trailing adapter strand and 3' abasic residue (red circle) through the pore limiting aperture after translocation of the tRNA.

Figure 6:
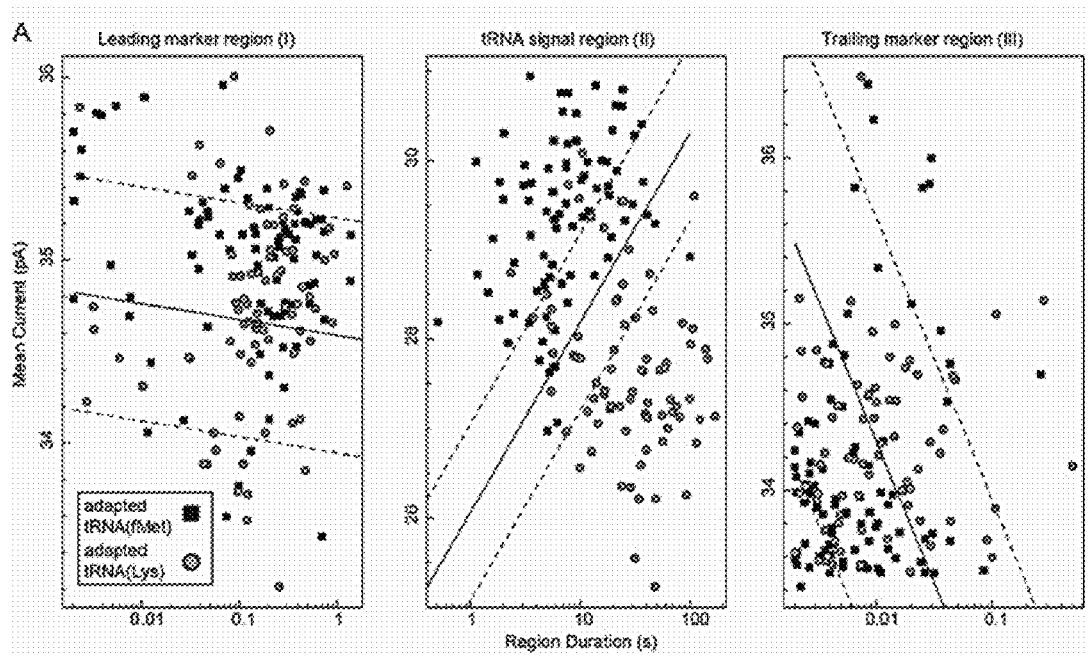

FIG. 6. Classification of tRNA molecules using duration and mean ionic for regions 1111 of adapted tRNA translocation events. We collected complete ionic current events (approx. 80 for each class) from experiments (n>=5) using adapted E. coli tRNA fMet (blue squares) or adapted tRNA Lys (magenta circles). In our model (FIG. 5C), region I and III correspond to the common leading and trailing marker regions, respectively, and region II corresponds to the intervening RNA dependent portion of the signal. The x axis is the duration of a given region and the y axis is mean current for that region. In each panel the solid black line is a semi-logarithmic decision boundary established for that region using a soft margin Support Vector Machine (SVM) (see Method). SVM margins are shown as dashed lines. The associated classification accuracy for region II was 87.2±5.3%. The associated classification accuracies for region I and III were 60.0±6.9% and 59.4±7.0%, respectively. The SVM classification accuracy (mean and SD) was established using 5 fold validation (see Methods). Data for the two tRNA species were collected separately from at least five independent nanopore experiments.

The oligonucleotides of the adapters as described in the accompanying sequence listing are as follows: CTCAC-CTATCCTTCCACXCATACTATCATTATCTXTCA-GATCTCACTAUCUG GU (SEQ ID No. 1) for the 5' loading oligonucleotide, and p-GATXGTGAGATCT-GATTTTTTTTTTTTTTZ (SEQ ID No. 2) for the 3' oligonucleotide, where X indicates an abasic 1',2' dideoxyribose and Z is a triethylene glycol cholesterol. Bolded sequence indicates RNA. For adapters that had no abasic markers, the sequences used were p-GATAGTGAGATCT-GATTTTTTTTTTTTTTZ (SEQ ID No. 3), and CTCAC-CTATCCTTCCACTCATACTATCATTATCTCTCA-GATCTCACTAUCUG GU (SEQ ID No. 4) for the 3' and 5' strands respectively.

DETAILED DESCRIPTION OF THE INVENTION

The present invention encompasses an oligonucleotide adapter that can be attached to intact tRNAs. To slow tRNA translocation through the pore, the present inventors employed a non-catalytic protein "brake" that loads onto the adapter. This allows the present invention to be used to determine the direction of strand translocation and provide sufficient resolution to determine ionic current signal features associated with the translocating adapter and the tRNA.

Results presented here demonstrate that tRNA attached to such an adapter and modulated by a protein brake can be completely translocated through the αHL nanopore, and that E. coli tRNA fMet and tRNA Lys produce differentiable nanopore signals in this system.

The invention encompasses methods employing nanopores for determining the structure and sequence of tRNA, and also encompasses novel structures comprising a tRNA linked to cholesterol-linked DNA or RNA adapter oligonucleotides. The novel structures facilitate both concentrating of the adapted tRNA to the lipid bilayer of the nanopore device and efficient denaturation of the tRNA as it passes through the nanopore. The cholesterol-linked DNA or RNA adapter oligonucleotides are bound to the tRNA by enzymatic ligation. Additionally the cholesterol-linked DNA or RNA adapter oligos can function as a loading site for ϕ29 DNA polymerase (ϕ29 DNAP).

A method of the invention comprises attaching DNA or RNA "handles" to a tRNA molecule. These handles provide a means of manipulating the tRNA molecule, including unfolding its structure and acting as targets for attaching other molecules to the tRNA.

The tRNA adapter may have a general structure as shown below:

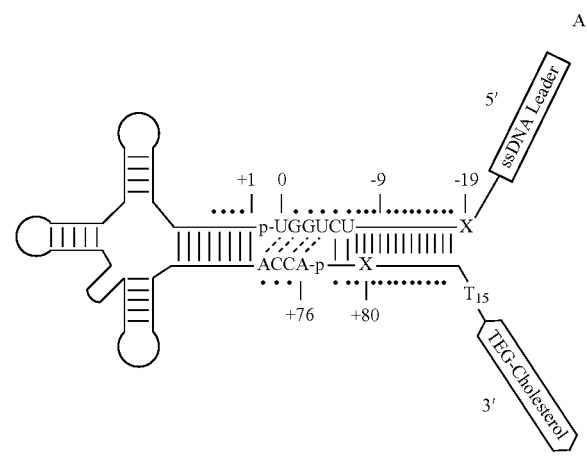

The invention encompasses a method for using a nanopore to detect individual tRNA molecules, which has applications in the study of structure and sequence of tRNA.

The method relies upon enzymatic ligation of cholesterol-linked DNA adapter oligonucleotides (Figure A) to the tRNA, which facilitates both concentrating of the adapted tRNA to the lipid bilayer of the nanopore device, and efficient denaturation of the tRNA as it passes through the nanopore. Additionally the DNA adapter can function as a loading site for ϕ29 DNA polymerase (ϕ29 DNAP).

The concept of the invention is as follows. The cholesterol-linked DNA adapter targets the universally conserved NCCA tail found at the 3' end of all mature tRNA with a complementary NGGU ribonucleotide overhang (Position −3 through 0 in Figure A).

In some embodiments, the inventors have also incorporated a double stranded region as shown in Fig. A, positions −19 through −4 with complementary positions at +77 through 90.

Additionally, the design as disclosed above may contain a single stranded DNA region (indicated as ssDNA Leader in Figure A) and a cholesterol tag (indicated as TEG-cholesterol in Figure A). The adapter region abutting the ACCA of the tRNA is phosphorylated to facilitate ligation of the adapter.

Abasic positions (apurinic/apyrimidinic) are optionally incorporated into the adapter strands to act as markers during subsequent analysis (indicated as X's in Fig A).

The adapter provides access to both the 5' and 3' ends of the tRNA. This potentially allows attachment of different kinds of molecules (such as cholesterol mentioned above) and can create sites for other molecules to interact with the tRNA (as in the case of φ29 DNA polymerase mentioned above).

In one embodiment the adapter can function as a handle for pulling or manipulating the tRNA, e.g., where the tRNA is captured in the nanopore (as above).

In another embodiment the adapter may incorporate other molecules such as fluorophores or other markers.

Embodiments

Capture and threading of tRNA through the αHL nanopore (any other nanopore may be used) is facilitated by ligation of at least one oligonucleotide adapter to the tRNA. Reading the nucleotide composition of individual tRNA molecules will require capture denaturation and threading of each strand sequentially through the nanopore. In initial experiments, it was found that native tRNA molecules caused long (>30 s) ionic current blockades of the αHL pore (data not shown). These molecules had to be ejected by voltage reversal to reestablish an open pore ionic current. This suggested that tRNA molecules in their native form would not readily translocate through the αHL nanopore.

The inventors reasoned that an extended single stranded region, longer than the ACCA in native tRNA, may be needed to initiate threading of each tRNA molecule into the lumen of αHL. To accomplish this, the inventors devised a strategy to covalently attach synthetic nucleic acid strands to the 3' and 5' ends of the tRNA. This was achieved using Y-shaped, partially double-stranded DNA-RNA adapter that contained a 3' RNA overhang complementary to the universally conserved CCA tail in tRNA (FIG. 1A).

The strand of the adapter, which bares the 3' RNA overhang, was designed to be ligated to the 5' end of a tRNA (referred to as the "leading strand"). The unpaired region of the leading strand contained 35 single stranded nucleotides and was designed to facilitate capture and threading into the nanopore. The double stranded region of the adapter was designed to allow a dsRNA ligation, and effectively extended the tRNA adapter stem by 15 base pairs.

The strand of the adapter that was designed to be covalently attached to the 3' end of the tRNA (referred to as the "trailing strand") incorporated a cholesterol tag at its 3' end. This was designed to locally concentrate the adapted tRNA at the lipid bilayer aqueous interface of the nanopore experimental setup. Association of the cholesterol moiety on the trailing strand with the bilayer favors capture of the free 5' end of the leading strand in the electric field surrounding the nanopore. Finally, the adapter design incorporates abasic residues into both leading and trailing strands to act as ionic current signal markers upstream and downstream of the ligated tRNA (FIG. 1A).

The inventors tested to determine if the adapter could be enzymatically ligated to tRNA using T4 RNA Ligase 2 (RNL2). Analysis of that ligation reaction revealed that a product of appropriate size ~160 nt was generated only in the presence of both the adapter and a model tRNA substrate (*S. cerevisiae* tRNA Phe) (FIG. 1B). These results indicated that enzymatic ligation with RNL2 was an effective method for adding adapter strands to this model tRNA.

To test this further, additional ligation experiments were performed with *E. coli* tRNA fMet. This tRNA represented a more challenging substrate because it contains a non-canonical nucleotide pair at the end of the acceptor stem (Raj Bhandary 1994).

Results showed that *E. coli* tRNA fMet was also a reactive substrate for ligation to the adapter. Initial nanopore experiments were performed with adapted *E. coli* tRNA fMet using an established single channel apparatus (see Methods) (FIG. 2A).

Ionic current blockade events were observed with a typical duration of tens of milliseconds (mean duration=10 2.6±0.06 sec, variation of the mean shown as SEM) (FIGS. 2B and 2C, magenta circles). These events were longer than the events observed for the adapter alone, which were typically a millisecond or less (mean duration=10 3.9±0.04 sec) (FIG. 2C, open triangles). The increased duration of events with adapted tRNA fMet suggested that longer or more structured molecules were being captured and translocated through the pore. The extremely short duration blockade events observed with the adapter alone were consistent with single stranded nucleic acids being translocated through the pore (Deamer and Branton 2002). It is reasoned that the longer dwell time was caused by tRNA, therefore conditions known to stabilize tRNA will increase event duration further.

Magnesium ions are known to stabilize the tertiary fold of tRNA (Stein and Crothers 1976; Serebrov et al. 2001). When magnesium chloride was added to the experimental buffer (5 mM final concentration) increase in event duration (100 fold or 2 Log 10 units) was observed relative to experiments absent magnesium (mean duration=10 1.4±0.1 sec) (FIG. 2C, blue squares). These blockades were self-terminating, as seen in experiments without magnesium. This result was consistent with capture of a magnesium stabilized tRNA. Together, these results suggested that the electric field driven denaturation of secondary, and potentially tertiary structure, facilitated the translocation of tRNA through the pore.

In one particular embodiment, φ29 DNAP acts as a molecular brake during translocation of adapted RNA under non-catalytic conditions. In previous studies with both RNA and DNA, uncontrolled polynucleotide translocation rate through a nanopore was too high to resolve single nucleotide level information about the translocating strand (Deamer and Branton 2002). Therefore the inventors sought to slow the translocation of adapted tRNA to improve resolution of tRNA features and to provide definitive evidence that adapted tRNA molecules transit the pore in their entirety. Control of DNA transit rates using DNA polymerases has been documented, and Lieberman et al. (2010) showed that φ29 DNAP can serve as a 'molecular brake' that controls the rate of DNA translocation through the αHL pore under noncatalytic conditions (absent Mg 2+ and dNTPs) (Lieberman et al. 2010). Furthermore, this molecular brake activity of φ29 DNAP has been observed on a chimeric DNA-RNA substrate with a nanopore device.

The inventors wanted to determine if the φ29 DNAP molecular brake could also be used to control translocation of RNA molecules containing more complex structures, such as stem-loops found in tRNA. For this the inventors synthesized a simple RNA hairpin, which the inventors ligated to the tRNA adapter (FIG. 3A). This synthetic RNA (referred to as RNA(hairpin)) mimicked the acceptor stem of tRNA fMet, where the two halves of the acceptor stem were linked by a short loop region of five uracil residues.

Nanopore capture of complexes formed between the adapted RNA and φ29 DNAP, similar to those seen by Lieberman et al., should result in greatly increased dwell time of individual adapted RNA molecules within the aperture of αHL. This would be observed as population of longer duration nanopore current blockades, which would be distinct from the shorter duration events of unbound adapted RNA strands. Control nanopore experiments with the adapted RNA(hairpin) construct absent φ29 DNAP resulted in current blockade events with mean duration on the order of milliseconds (mean duration=10 3.2±0.02 sec) (FIG. 3C, magenta circles). Addition of φ29 DNAP to the buffer solution containing adapted RNA(hairpin) on the cis side of the nanopore apparatus produced two different types of current blockade events. These events typically fell into one of two populations: a short duration population (duration<0.1 sec, mean 10 2.9±0.09 sec), similar to events in the control experiment, and a long duration population not seen in the control experiment (duration>=0.1 sec, mean 10 0.43±0.03 sec) (FIGS. 3B and 3C, blue triangles). The shorter duration population (<0.1 s) appeared consistent with RNA(hairpin) absent φ29 DNAP and was statistically indistinguishable from the event population seen in the control (p value<0.66, 2 tailed Ttest). The longer duration population (>=0.1 s) was longer in mean duration and was statistically different from the population seen in the control (p value<0.0001, 2 tailed Ttest). This suggested that these long duration events were the result of φ29 DNAP binding the adapted RNA substrate and slowing strand translocation through the nanopore.

The inventors included two abasic residues (1'H deoxyribose) in the adapter strands near the ligation junctions with the RNA to act as indicators of strand translocation (see FIG. 3A). Abasic residues have been shown to cause distinctive high current spikes that are apparent during enzyme controlled translocation of oligonucleotides through the αHL pore (Gyarfas et al. 2009; Lieberman et al. 2010). Because the abasic residues in the adapter (subsequently referred to as a "dualabasic adapter") flank the RNA insert, they should translocate through the nanopore before and after the RNA insert (FIG. 4A). This should produce an ionic current trace with high current spikes bracketing an intervening region and indicate strand translocation occurred in a linear conformation. Further, the intervening region would correspond to the RNA (hairpin) insert traversing the pore.

As predicted, translocation of dual-abasic adapted RNA (hairpin) bound to φ29 DNAP resulted in blockade events containing two distinct ionic current spikes in the range of 33.5 pA to 36.5 pA (FIG. 4B). This suggested that the adapted RNA hairpin translocated completely through the nanopore, and that φ29 DNAP acted as a passive molecular brake for both the DNA and RNA portions of the chimeric molecule.

Further experiments found that the ionic current pattern produced by 5' and 3' abasic residues establishes the direction of translocation and indicates complete strand translocation. To establish the direction that φ29 DNAP bound strands translocated through the nanopore, it was necessary to assign each of the observed high current spikes to either the 5' or 3' abasic residue. To do this the inventors synthesized adapters that contained only one of the 5' or 3' abasic residues. These "monoabasic adapters" were ligated to the RNA(hairpin) substrate (see FIG. 3A). Substrates bearing the 5' monoabasic adapter typically produced events containing a single high current spike (33.536.5 pA) near the beginning of the event (FIG. 4C). Substrates bearing the 3' mono abasic adapter caused a similar high current spike near the end of the event, which was preceded by a low current state (<=26.5 pA) (FIG. 4D). These observations provided an ionic current model for complete translocation of the dual abasic adapted RNA (hairpin) in the 5' to 3' direction. That is, the 5' abasic residue caused the first high current spike, which was followed by the intervening current region corresponding to the RNA, which includes the low current state. This is followed by the high current spike proximal to the end of the event that is caused by the 3' abasic residue.

Using this model, the inventors quantified the frequency of the leading and trailing high current spikes (henceforth referred to as leading and trailing markers) in events greater than is duration. Translocation of the dualabasic adapted RNA resulted in 27.4% of events (102 of 372) that contained both the leading marker and trailing marker separated by a region containing a low current segment (Table 1). An additional 43% of events were classified as containing only a leading marker and 6.7% were classified as containing only a trailing marker. The disparity in frequency between leading and trailing markers suggested that the 3 end of the strand was more difficult to resolve.

One explanation for this discrepancy was that that both abasic residues passed through the nanopore, but the trailing marker was more difficult to detect. To test this explanation the inventors determined the fraction of events in which they observed high current markers in the mono abasic adapter data. Translocation of strands bearing the 5' mono abasic adapter produced events with a single high current spike 64.5% of the time (Table 1). Similar analysis of 3' mono abasic adapter data produced a smaller fraction of events (37.9%) with a single high current spike (Table 1). This result showed that the 3' abasic residue was in fact more difficult to resolve.

Together these results demonstrate that the dualabasic adapted RNA (hairpin) substrate was transiting the pore in the 5' to 3' direction when bound by φ29 DNAP. The abasic residues produced distinctive markers for the adapted RNA entering and exiting the nanopore. From this the inventors inferred that the adapted RNA(hairpin) strand translocated through the nanopore in its entirety when both of these markers were observed. Further, these markers should provide approximate boundaries of the RNA dependent portion of the nanopore signal.

In a further experiment it was found that *E. coli* tRNA fMet and tRNA Lys can be classified based on their nanopore current signals. If the ionic current segment flanked by the high current markers contains the RNA dependent portion of nanopore signal, then that region should differentiate tRNA species. Further, a tRNA specific change seen in the putative RNA dependent region, when bordered by the adapter dependent marker regions, would be evidence that the adapted tRNA translocated entirely through the nanopore. The inventors used the φ29 DNAP mediated braking method, as had been done with the RNA (hairpin) substrate, to improve temporal resolution of adapted tRNA. For this experiment the inventors selected two well characterized tRNA species for nanopore analysis, *E. coli* tRNA fMet and *E. coli* tRNA Lys. These tRNAs exist in the *E. coli* genome as either a single isoform (tRNA Lys) or as two isoforms that differ by only a single nucleotide (tRNA fMet) (Raj Bhandary 1994). Additionally, tRNA Lys and tRNA fMet have similar lengths (76nt and 77nt respectively), but have significantly different nucleotide compositions (50.0% GC and 64.9% GC content respectively) and would be expected to generate different ionic current signal.

Experiments with the adapted tRNA fMet substrate produced 85 events that contained the leading and trailing markers bracketing an extended intervening current region (17.6% of 481 total events) (FIG. 5A). Experiments with the adapted tRNA Lys substrate produced 77 events that contained the leading and trailing markers also bracketing an extended intervening current region (22.3% of 348 total events) (FIG. 5B). As suggested by the results with the adapted RNA(hairpin) substrate, these events were presumed to result from complete translocation of the adapted tRNA through the nanopore. These events were selected for further analysis of tRNA specific ionic current signal. To test the putative RNA dependent region for tRNA specific signal (see FIG. 5AB, Region II), the inventors segmented the ionic current signal from each translocation event into regions I through III. As was the case for the RNA (hairpin) substrate (see FIG. 4), regions I and III included the leading and trailing markers respectively, which corresponded to the 5' and 3' abasic residues of the adapter translocating through the nanopore. These served as control regions for our analysis (FIG. 5C). Bracketed by these markers, Region II was expected to change based on the identity of the tRNA. Initial inspection of ionic current parameters, mean current and dwell time, suggested that Region II provided the best discrimination between tRNA fMet and tRNA Lys (FIG. 6). As expected, mean current and duration for regions I and III did not appear to differ between tRNA fMet and tRNA Lys.

To quantitatively assess the influence of tRNA type on ionic current, the inventors analyzed the data in FIG. 6 using a soft margin support vector machine (SVM) (Cortes and Vapnik 1995). A SVM was used to quantify the discrimination between the two tRNA species using their ionic current parameters in each of the three regions. The SVM produced an optimal linear decision boundary for the event log durations and mean currents plotted in FIG. 6. The inventors used Sway cross validation to calculate classification accuracy (mean and SD) of the boundaries produced for each of the regions (see Methods). Regions I and III provided discrimination between the two tRNA only slightly better than chance at 60.0±6.9% and 59.4±7.0% accuracy, respectively. In contrast, Region II provided a classification accuracy of 87.2±5.3%. This result demonstrated quantitatively that tRNA contributed to the nanopore signal in Region II. Further, because the RNA-dependent region II was preceded and followed by adapter-dependent regions I and III, the inventors concluded that adapted tRNA translocated completely through the nanopore.

In summary, the inventors have shown that individual biological tRNA molecules can be unfolded and translocated through a nanopore as linear strands. To facilitate this the inventors developed a double stranded oligonucleotide adapter that can be enzymatically ligated to biological tRNA. The two strands of the adapter act to locally concentrate adapted tRNA at the bilayer and to initiate strand threading through the nanopore.

Using φ29 DNAP under non-catalytic conditions, the inventors were able to slow strand translocation through the pore. This allowed observation of adapted tRNA translocating 5' to 3' through the pore as a linear strand. Finally, as evidence that tRNA influenced ionic current during translocation, the inventors have shown that E. coli tRNA fMet and tRNA Lys produced differentiable ionic current signals. Linear translocation of biological tRNA through the nanopore is a first step towards single molecule direct sequence analysis of tRNA.

Full implementation of a nanopore-based RNA sequencing method may benefit from coupling an active molecular motor to translocate tRNA, as has been accomplished for DNA sequencing using φ29 DNAP in a catalytic mode.

Use of multichannel nanopore devices will allow for reading tens of thousands of individual tRNA molecules and the inventors expect that a mature nanopore-based method for directly sequencing individual tRNA molecules will yield both canonical base identity and nucleotide modification states along entire strands.

Exemplary Embodiment: Adapter Design and Hybridization

The oligonucleotides of the adapters were designed with the complementary sequences CTCACCTATCCTTC-CACXCATACTATCATTATCTXTCAGATCT-CACTAUCUGG U (SEQ ID No. 1) for the 5' loading oligonucleotide, and p-GATXGTGAGATCT-GATTTTTTTTTTTTTTZ (SEQ ID No. 2) for the 3' oligonucleotide, where X indicates an abasic 1',2' dideoxyribose and Z is a triethylene glycol cholesterol. Bolded sequence indicates RNA. For adapters that had no abasic markers, the sequence used were p-GATAGTGAGATCT-GATTTTTTTTTTTTTTZ (SEQ ID No. 3), and CTCAC-CTATCCTTCCACTCATACTATCATTATCTCTCA-GATCTCACTAUCUGG U (SEQ ID No. 4) for the 3' and 5' strands respectively.

To form the adapter the complementary 5' and 3' adapter strands were hybridized at 100 μM in 10 mM TRIS pH 8 and 50 mM NaCl by heating to 95° C. for thirty second and allowed to cool to room temperature.

Adapters were ligated to mature tRNA using T4 RNA Ligase 2 using a standard protocol.

ADVANTAGES OF THE INVENTION

The adapter of the invention allows tRNAs to be manipulated, which is notoriously difficult. tRNA form very stably folded structures, which can be difficult to unravel, and because of the compact structure tRNA form, reverse transcription is difficult to accomplish. By annealing adapter handles, the tRNA can be easily unfolded. The adapters can also potentially function as a landing site for primers.

Methods

Oligonucleotide Synthesis and Purification

All oligonucleotides were synthesized by the Stanford Protein and Nucleic Acids facility (PAN) using standard phosphoramidite chemistry. Oligonucleotides were purified by denaturing 7M urea polyacrylamide gel electrophoresis (PAGE) in 1×TBE, followed by overnight elution from an excised band at 4° C. in 300 mM Sodium Acetate pH 5.2 and 1 mM EDTA. DNA was precipitated and recovered by adding 100% molecular biology grade ethanol (Sigma Aldrich) to 70% final v/v and centrifuged for 30 minutes at 14,000×g for and 4° C. Alternately, RNA containing oligonucleotides were recovered by precipitation in 75% ethanol v/v and centrifuged at 14,000×g for 30 minutes at 4° C. The ethanol mixture was aspirated and oligonucleotides were then washed with an equal volume of 70% or 75% ethanol and pelleted again for 10 minutes at 14,000×g and 4° C. Ethanol was aspirated and the pellets were allowed to dry under vacuum to remove residual ethanol. Oligonucleotides were then resuspended in nuclease free water, quantified by Nanodrop (Thermo Scientific), and stored at 80° C.

Adapter Design and Hybridization

5' leading strand oligonucleotide (Bolded italicized bases indicate RNA; plain letters are DNA, X indicates an abasic 1'H deoxyribose): 5'CTCACCTATCCTTCCACXCATAC-TATCATTATCTXTCAGATCTCACTAUCUGGU3'

3' trailing strand oligonucleotide (X indicates an abasic 1',2' dideoxyribose; Z is a triethylene glycol cholesterol): 5'phosGATXGTGAGATCTGATTTTTTTTTTTTTTZ3'.

For adapter strands that had no abasic marker the sequences used were: 5'CTCACCTATCCTTCCACTCATACTATCAT- TATCTCTCAGATCTCACTAUCUGGU3' and 5'phosGA-TAGTGAGATCTGATTTTTTTTTTTTTTZ3'. Adapters were formed by combining leading and trailing strands at 100 μM in 10 mM TrisHCl pH 8 and 50 mM NaCl. The mixture was heated to 95° C. for thirty seconds and allowed to cool to room temperature.

RNA, RNA Ligation Reaction, and Purification of Full Length Products

E. coli tRNA Lys and tRNA fMet were purchased from Sigma Aldrich. The RNA hairpin control was prepared by the Stanford PAN facility using the sequence 5'phosCGCGGGGUUUUUCCCCGCAACCA3' (SEQ ID NO:5). RNA substrates were ligated to adapters using RNA Ligase 2 (NEB). Ligation reactions were carried out in 20 μl of buffer recommended by the manufacturer supplemented with 0.5 mM ATP, 5% PEG 8000, and 2 μM each of RNA and adapter. To end the reaction and prepare the sample for purification, 50 μL urea loading buffer (7M urea and 0.1× TBE) was added to the sample and heated to 95° C. for 5 minutes. The products were separated on a 7M urea PAGE gel in 1×TBE. The gel was post-stained with 2×SybrGold (Life Technologies) and product of appropriate size for the complete ligation product was excised. Ligated RNA were recovered by electroelution into 3.5 kDa MWCO Dtubes (Novagen) at 100V for 2 hours in 1×TBE. Recovered ligated RNA preparations were ethanol precipitated, quantified by Nanodrop (Thermo Scientific), and stored at 80° C.

Nanopore Experiments

Nanopore experiments were performed using a single αHL nanopore embedded in a planar 1,2diphytanoylsyn-glycerophosphatidylcholine bilayer using an apparatus described previously (Akeson et al. 1999). Experiments were conducted in 0.3M KCl and 10 mM HEPE pH 8.0 at 28° C. (+/0.4 C) at 180 mV (trans well positive). Dithiothreitol (2 mM final) and EDTA pH 8.0 (1 mM final) were added to the well on the cis side of the bilayer. In the case of experiments looking at the effect of Mg 2+, MgCl 2 was added to the buffer to 5 mM an EDTA was omitted from the cis side well. Nucleic acid substrates were added to 0.5 nM unless otherwise noted to the cis well and allowed to incubate two minutes to associate with the bilayer. For experiments where φ29 DNAP was to be added, an additional 12.5 minute incubation was allowed; during this period we observed captures of unbound RNA substrate prior to adding φ29 DNAP (Enzymatics) to 75 nM. Ionic current measurements were collected with an Axon Axopatch 200B (Molecular Devices) patch clamp amplifier in whole cell, voltage clamped mode and filtered with an analog low pass Bessel filter at 5 kHz, then digitized using an Axon Digidata 1440A analog to digital converter (Molecular Devices) at 100 kHz bandwidth.

Event Detection and Ionic Current Region Measurements

For nanopore experiments that examined populations of ionic current blockade events a custom developed event detection program was used (PyPore). The detection algorithm identified ionic current blockades that were self-terminating by selecting for segments that deflected from open nanopore current (68.572. pA) below a cutoff of 45 or 55 pA and with a minimum duration>0.1 millisecond, where voltage was not reversed to eject the stand from the pore (current never<0 pA). For experiments where individual ionic current blockade events were examined, raw nanopore ionic current data was filtered with a digital 2 kHz low pass Bessel filter and analyzed using Clampfit 10.4 (Molecular Devices). For φ29 DNAP molecular braking experiments, events were selected from current blockades that had durations greater than one second and self-terminated Event classification from adapted RNA (hairpin) substrates were analyzed as articulated in the text. For adapted tRNA data, complete translocation events were selected based on the criteria that they contained exactly two abasic-dependent regions; these were defined as high current regions with a mean current greater than 33.5 pA, less than 36.5 pA, and minimum a duration greater than 2 ms. After selection as complete translocation events, duration and mean current for states IIII was measured by hand using Clampfit's internal statistics measuring program.

Semilogarithmic Decision Boundary and Accuracy Derivation.

Event durations were transformed to log durations (log 10) and a linear decision boundary was established using the kernlab (v 0.919) package (Karatzoglou et al. 2004) under R (v 3.0.2). The ksvm parameters used were "type='Csvc', kernel='vanilladot', C=10" to produce a soft margin decision boundary. To assess classification accuracy, a fivefold training/test regimen was used. The data set was shuffled and then partitioned into 5 groups of nearly equal size. In a series of 5 tests, one of the 5 groups was withheld as a test set, while the decision boundary was calculated using the remaining 4. This was repeated for each of the 5 groups. This procedure was repeated 50 times, providing 250 assessments of accuracy. Mean and standard deviation of these 250 accuracy scores are reported. For this study, we used a balanced accuracy score, calculated as the mean recall rate for each of the two data classes. For two classes with labels $\{1, 1\}$, balanced accuracy=[pred(1)/true(1)+pred(−1)/true(−1)]/2 where true(n) are counts of test data labeled n, and pred(n) are counts of test data that are correctly classified. The graphic provided in FIG. 6 was derived using the full dataset and the kernlab package with parameters as above. Margins (dotted lines) in FIG. 6 provide the optimized bounds that maximize the proper classification of labeled data outside the margin while minimizing the he cost of misclassified data on the "wrong" side of that margin (Cortes and Vapnik 1995).

TABLE 1

RNA(hairpin) nanopore translocation events classified by detection of leading and trailing high current markers. All events were >=1 s duration.

| Substrate | Events | Leading and trailing high current observed[a] | Leading high current observed[b] | Trailing high current observed[c] | Other events[d] |
|---|---|---|---|---|---|
| RNA(hairpin) (dual-abasic adapter) | 372 | 102 (27.4%) | 160 (43.0%) | 25 (6.7%) | 85 (22.9%) |
| RNA(hairpin) (5' mono-abasic adapter) | 287 | 3 (1.0%) | 185 (64.5%) | 10 (3.5%) | 89 (31.0%) |
| RNA(hairpin) (3' mono-abasic adapter) | 285 | 3 (1.1%) | 4 (1.4%) | 108 (37.9%) | 170 (59.6%) |

[a]These events contained three required features as illustrated in FIG. 4: 1) a high current marker segment (mean current 33.5-36.5 pA with >=2 ms duration); 2) a low current segment (mean current =<26.5 pA with >=10 ms); 3) a second high current segment proximal to the termination of the event.
[b]These events contained: 1) a single high current marker segment (mean current 33.5-36.5 pA with duration >=2 ms); 2) a low current segment (mean current =<26.5 pA with >=10 ms) that always followed the high current marker.
[c]These events contained: 1) a single high current marker segment (mean current 33.5-36.5 pA with duration >=2 ms); 2) a low current segment (=<26.5 pA with a duration of 10 ms) that always preceded the high current marker segment.
[d]Events classified as "other" included all events that could not be assigned to one of the other categories, such as those displaying more than two high current marker segment and events displaying no high current marker segments.

General Disclosures and Definitions

All publications disclosed herein are hereby incorporated by reference for all purposes. As used in this specification, the singular forms "a, an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. The term "consisting essentially of" is used herein to mean that, in addition to the features specifically identified, other features may be present which do not materially alter the claimed invention.

The terms "complementary" and "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands.

"Conservative amino acid substitutions" are those substitutions that, when made, least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The term "derivative" refers to the chemical modification of a polypeptide sequence, or a polynucleotide sequence. Chemical modifications of a polynucleotide sequence can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "fragment" is a unique portion of a parent sequence which is identical in sequence to but shorter in length than the parent sequence. A fragment may comprise up to the entire length of the defined sequence, minus one nucleotide/amino acid residue. For example, a fragment may be at least 5, 10, 15, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50% of a polypeptide) as shown in a certain defined sequence. Clearly these lengths are exemplary, and any length that is supported by the specification, including the Sequence Listing, tables, and figures, may be encompassed by the present embodiments.

The phrases "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151-153 and in Higgins, D. G. et al. (1992) CABIOS 8:189-191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequence pairs. Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403-410). The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.9 (May 7, 1999) set at default parameters. Such default parameters may be, for example: Matrix: BLOSUM62; Reward for match: 1; Penalty for mismatch: −2; Open Gap: 5 and Extension Gap: 2 penalties; Gap x drop-off: 50; Expect: 10; Word Size: 11; Filter: on.

Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the hydrophobicity and acidity at the site of substitution, thus preserving the structure (and therefore function) of the polypeptide. Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Hybridization" refers to the process by which a polynucleotide strand anneals with a complementary strand through base pairing under defined hybridization conditions. Specific hybridization is an indication that two nucleic acid sequences share a high degree of identity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml denatured salmon sperm DNA.

Generally, stringency of hybridization is expressed, in part, with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook et al., 1989, *Molecular Cloning: A Laboratory Manual*, $2^{nd}$ ed., vol. 1-3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, denatured salmon sperm DNA at about 100-200 µg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with the second nucleic acid sequence. For instance, a promoter is operably linked to a coding sequence if the promoter affects the transcription or expression of the coding sequence. Generally, operably linked DNA sequences may be in close proximity or contiguous and, where necessary to join two protein coding regions, in the same reading frame.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

REFERENCES

All references are incorporated by reference.

Church, G. M.; Deamer, D. W., Branton, D., Baldarelli, R., Kasianowicz, J. (1998). "U.S. Pat. No. 5,795,782 (filed March 1995) Characterization of individual polymer molecules based on monomer-interface interaction".

Kasianowicz, J J; Brandin E, Branton D, Deamer D W (1996-11-26). "Characterization of individual polynucleotide molecules using a membrane channel.". Proc Natl Acad Sci USA 93 (24): 13770-3. doi:10.1073/pnas.93.24.13770. PMC 19421. PMID 8943010.

Garaj S, Hubbard W, Reina A, Kong J, Branton D, Golovchenko J (September 2010). "Graphene as a sub-nanometer trans-electrode membrane". Nature 467 (7312): 190-3. doi:10.1038/nature09379. PMID 20720538.

Clarke J, Wu H C, Jayasinghe L, Patel A, Reid A, Bayley H (2009). "Continuous base identification for single-molecule nanopore DNA sequencing". Nature Nanotechnology 4 (4): 265-270. doi:10.1038/nnano.2009.12. PMID 19350039.

Kasianowicz J, Brandin E, Branton D, Deamer D (1996). "Characterization of individual polynucleotide molecules using a membrane channel". Proc. Natl. Acad. Sci. USA 93: 1377-13773.

Stoddart D, Heron A, Mikhailova E, Maglia G, Bayley H (2009). "Single-nucleotide discrimination in immobilized DNA oglionucleoties with a biological nanopore". Proc. Natl. Acad. Sci. USA 106: 7702-7707.

Purnell R, Mehta K, Schmidt J (2008). Nucleotide identification and orientation discrimination of DNA homopolymers immobilized in a protein nanopore" Nano Letters 8 (9) 3ɸ29-3034.

Stoddart D, Maglia G, Mikhailova E, Heron A, Bayley H (2010). "Multiple base-recognition sites in a biological nanopore: two heads are better than one." Angew. Chem. 49: 556-559.

Manrao E, Derrington I, Pavlenok M, Niederweis M, Gundlach J (2011). "Nucleotide discrimination with DNA immobilized in the MspA nanopore." PLoS ONE 6 (10).

Jump up^ Faller M, et al. (2004) "The structure of a mycobacterial outer-membrane channel." Science.

Butler T Z, Pavlenok M, Derrington I, Niederweis M, Gundlach J (2008). "Single-molecule DNA detection with an engineered MspA protein nanopore." Proc. Natl. Acad. Sci 106 (9) 20647-20652.

McNally B, Singer A, Yu Z, Sun Y, Weng Z, Meller A (2010). "Optical recognition of converted DNA nucleotides for single molecule DNA sequencing using nanopore arrays." Nano Lett. 10 (6): 2237-2244.

Soni G, Singer, A, Yu Z, Sun Y, McNally B, Meller A (2010). "Synchronous optical and electrical detection of biomolecules traversing through solid-state nanopores." Rev. Sci. Instrum. 81.

Chang S, Huang S, He J, Liang F, Zhang P, Li S, Chen X, Sankey O, Lindsay S (2010). "Electronic signatures of all four DNA nucleosides in a tunneling gap." Nano Lett. 10: 1070-1075.

Sadki E S, Garaj S, Vlassarev D, Golovchenko J A, Branton D (2011). "Embedding a carbon nanotube across the diameter of a solid state nanopore." J. Vac. Sci. Technol. 29 (5).

Winters-Hilt, S; Vercoutere W, DeGuzman V S, Deamer D, Akeson M, Haussler D (February 2003). "Highly accurate classification of Watson-Crick basepairs on termini of single DNA molecules". Biophys J. 84 (2 Pt 1): 967-76. doi:10.1016/50006-3495(03)74913-3. PMC 1302674. PMID 12547778.

Stoddart D, Maglia G, Mikhailova E, Heron A, Bayley H (2010). "Multiple Base-Recognition Sites in a Biological Nanopore: Two Heads are Better than One". Angew Chem Int Ed Engl 49 (3): 556-9. doi:10.1002/anie.200905483. PMID 20014084.

Rusk, Nicole (2009-04-01). "Cheap Third-Generation Sequencing". Nature Methods 6 (4): 244-245. doi:10.1038/nmeth0409-244a.

The invention claimed is:

1. A method for sequencing tRNA, the method comprising
(1) providing a nanopore immersed in an ionic solution,
(2) providing a tRNA,
(3) covalently ligating at least one oligonucleotide adapter to the tRNA,
(4) capturing and threading the tRNA within the nanopore, and
(5) measuring an ionic current through the nanopore wherein when a molecule passes through or near to the nanopore, it creates a characteristic perturbation of the current signature passing between two sides of the nanopore,
wherein said at least one oligonucleotide adapter is attached at both the 3' end and the 5' end of the tRNA, and wherein said at least one oligonucleotide adapter is a Y-shaped, partially double-stranded DNA-RNA adapter that contained a 3' RNA overhang complementary to the universally conserved CCA tail in tRNA.

2. The method of claim 1 wherein the oligonucleotide adapter incorporates a cholesterol tag within its 3' end.

3. The method of claim 1 wherein the oligonucleotide adapter is ligated to the tRNA using T4 RNA Ligase.

4. A method for sequencing tRNA, the method comprising
(1) providing a nanopore immersed in an ionic solution,
(2) providing a tRNA,
(3) covalently ligating at least one oligonucleotide adapter to the tRNA,
(4) capturing and threading the tRNA within the nanopore,
(5) measuring an ionic current through the nanopore wherein when a molecule passes through or near to the nanopore, it creates a characteristic perturbation of the current signature passing between two sides of the nanopore, wherein the oligonucleotide adapter comprises a sequence having at least 80% sequence identity to: CTCACCTATCCTTCCACXCATACTATCAT-TATCTXTCAGATCTCACTAUCUGGU (SEQ ID No. 1) wherein X indicates an abasic 1'2' dideoxyribose, and wherein italicized sequence indicates RNA.

5. A method for sequencing tRNA, the method comprising
(1) providing a nanopore immersed in an ionic solution,
(2) providing a tRNA,
(3) covalently ligating at least one oligonucleotide adapter to the tRNA,
(4) capturing and threading the tRNA within the nanopore, (5) measuring an ionic current through the nanopore wherein when a molecule passes through or near to the nanopore, it creates a characteristic perturbation of the current signature passing between two sides of the nanopore, wherein the oligonucleotide adapter comprises a sequence having at least 80% sequence identity to: p-GATXGTGAGATCTGATTTTTTTTTTTTTTZ (SEQ ID No. 2) wherein X indicates an abasic 1'2' dideoxyribose and Z is a triethylene glycol cholesterol.

6. A method for sequencing tRNA, the method comprising
(1) providing a nanopore immersed in an ionic solution,
(2) providing a tRNA,
(3) covalently ligating at least one oligonucleotide adapter to the tRNA,
(4) capturing and threading the tRNA within the nanopore,
(5) measuring an ionic current through the nanopore wherein when a molecule passes through or near to the nanopore, it creates a characteristic perturbation of the current signature passing between two sides of the nanopore, wherein the oligonucleotide adapter comprises a sequence having at least 80% sequence identity to: p-GATAGTGAGATCTGATTTTTTTTTTTTTTZ (SEQ ID No. 3) for the 3' strand.

7. A method for sequencing tRNA, the method comprising
(1) providing a nanopore immersed in an ionic solution,
(2) providing a tRNA,
(3) covalently ligating at least one oligonucleotide adapter to the tRNA,
(4) capturing and threading the tRNA within the nanopore,
(5) measuring an ionic current through the nanopore wherein when a molecule passes through or near to the nanopore, it creates a characteristic perturbation of the current signature passing between two sides of the nanopore, wherein the oligonucleotide adapter comprises a sequence having at least 80% sequence identity to: CTCACCTATCCTTCCACTCATACTATCATTATCTCTCAGATCTCACTAUCUGGU (SEQ ID No. 4) for the 5' strand.

8. The method of claim 1 wherein the step of covalently ligating is performed by hybridizing the at least one oligonucleotide adapter at 100 µM in 10 mM TRIS pH 8 and 50 mM NaCl by heating to 95° C. for thirty seconds and allowed to cool to room temperature.

9. A method for sequencing tRNA, the method comprising
(1) providing a nanopore immersed in an ionic solution,
(2) providing a tRNA,
(3) covalently ligating at least one cholesterol-linked DNA or RNA oligonucleotide adapter to the tRNA,
(4) capturing and threading the tRNA within the nanopore,
(5) measuring an ionic current through the nanopore wherein when a molecule passes through or near to the nanopore, it creates a characteristic perturbation of the current signature passing between two sides of the nanopore, wherein the cholesterol-linked DNA or RNA adapter oligonucleotide comprises a sequence having at least 80% sequence identity to: p-GATXGTGAGATCTGATTTTTTTTTTTTTTZ (SEQ ID No. 2) wherein X indicates an abasic 1'2' dideoxyribose and Z is a triethylene glycol cholesterol.

10. A method for sequencing tRNA, the method comprising
(1) providing a nanopore immersed in an ionic solution,
(2) providing a tRNA,
(3) covalently ligating at least one cholesterol-linked DNA or RNA oligonucleotide adapter to the tRNA,
(4) capturing and threading the tRNA within the nanopore,
(5) measuring an ionic current through the nanopore wherein when a molecule passes through or near to the nanopore, it creates a characteristic perturbation of the current signature passing between two sides of the nanopore, wherein the cholesterol-linked DNA or RNA adapter oligonucleotide comprises a sequence having at least 80% sequence identity to: p-GATAGTGAGATCTGATTTTTTTTTTTTTTZ (SEQ ID No. 3) for the 3' strand.

11. A method for sequencing tRNA, the method comprising
(1) providing a nanopore immersed in an ionic solution,
(2) providing a tRNA,
(3) covalently ligating at least one cholesterol-linked DNA or RNA oligonucleotide adapter to the tRNA,
(4) capturing and threading the tRNA within the nanopore,
(5) measuring an ionic current through the nanopore wherein when a molecule passes through or near to the nanopore, it creates a characteristic perturbation of the current signature passing between two sides of the nanopore, wherein the cholesterol-linked DNA or RNA adapter oligonucleotide comprises a sequence having at least 80% sequence identity to: CTCACCTATCCTTCACTCATACTATCATTATCTCTCAGATCTCACTAUCUGGU (SEQ ID No. 4) for the 5' strand.

12. The method of claim 1 wherein the nanopore comprises αHL.

13. The method of claim 1 wherein said at least one oligonucleotide adapter is synthetic.

14. The method of claim 1 wherein said at least one oligonucleotide adapter is non-naturally-occurring.

* * * * *

SEQUENCE LISTING

```
<160> NUMBER OF SEQ ID NOS: 5

<210> SEQ ID NO 1
<211> LENGTH: 54
<212> TYPE: DNA
<213> ORGANISM: Artificial Sequence
<220> FEATURE:
<223> OTHER INFORMATION: 5' leading strand oligonucleotide; 6
      nucleotides at 3' end are RNA
<220> FEATURE:
<221> NAME/KEY: misc_feature
<222> LOCATION: (18)..(18)
<223> OTHER INFORMATION: n is an abasic 1',2' dideoxyribose
<220> FEATURE:
<221> NAME/KEY: misc_feature
<222> LOCATION: (35)..(35)
<223> OTHER INFORMATION: n is an abasic 1',2' dideoxyribose

<400> SEQUENCE: 1
ctcacctatc cttccacnca tactatcatt atctntcaga tctcactauc uggu          54

<210> SEQ ID NO 2
<211> LENGTH: 30
<212> TYPE: DNA
```

```
<213> ORGANISM: Artificial Sequence
<220> FEATURE:
<223> OTHER INFORMATION: 3' trailing strand oligonucleotide
<220> FEATURE:
<221> NAME/KEY: misc_feature
<222> LOCATION: (4)..(4)
<223> OTHER INFORMATION: n is an abasic 1',2' dideoxyribose

<400> SEQUENCE: 2
gatngtgaga tctgattttt ttttttttt                                30

<210> SEQ ID NO 3
<211> LENGTH: 30
<212> TYPE: DNA
<213> ORGANISM: Artificial Sequence
<220> FEATURE:
<223> OTHER INFORMATION: 3' trailing strand oligonucleotide

<400> SEQUENCE: 3
gatagtgaga tctgattttt ttttttttt                                30

<210> SEQ ID NO 4
<211> LENGTH: 54
<212> TYPE: DNA
<213> ORGANISM: Artificial Sequence
<220> FEATURE:
<223> OTHER INFORMATION: 5' leading strand oligonucleotide; 6
      nucleotides at 3' end are RNA

<400> SEQUENCE: 4
ctcacctatc cttccactca tactatcatt atctctcaga tctcactauc uggu    54

<210> SEQ ID NO 5
<211> LENGTH: 23
<212> TYPE: RNA
<213> ORGANISM: Artificial Sequence
<220> FEATURE:
<223> OTHER INFORMATION: RNA hairpin control

<400> SEQUENCE: 5
cgcgggguuu uuccccgcaa cca                                      23
```